US00PP14694P29

(12) United States Plant Patent
Hofmann

(10) Patent No.: US PP14,694 P2
(45) Date of Patent: Apr. 13, 2004

(54) NEW GUINEA IMPATIENS PLANT NAMED 'FISNICS FLAME'

(50) Latin Name: *Impatiens hawkeri*
Varietal Denomination: Fisnics Flame

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/453,125

(22) Filed: Jun. 3, 2003

(51) Int. Cl.[7] ..... A01H 5/00

(52) U.S. Cl. ..... Plt./318

(58) Field of Search ..... Plt./318

*Primary Examiner*—Kent Bell
(74) *Attorney, Agent, or Firm*—C. A. Whealy

(57) ABSTRACT

A new and distinct cultivar of New Guinea Impatiens plant named 'Fisnics Flame', characterized by its outwardly spreading and uniformly mounded plant habit; medium to tall growth habit; freely branching and freely flowering habit; dark green-colored foliage; and medium to large, somewhat rounded, bright orangish red-colored flowers that are positioned just above and beyond the foliage.

1 Drawing Sheet

Botanical classification/cultivar designation: *Impatiens hawkeri* cultivar Fisnics Flame.

BACKGROUND OF THE INVENTION

The present Invention relates to a new and distinct cultivar of New Guinea Impatiens plant, botanically known as *Impatiens hawkeri,* and hereinafter referred to by the name 'Fisnics Flame'.

The new Impatiens is a product of a planned breeding program conducted by the Inventor in Hillscheid, Germany and Galder, Gran Canaria, Spain. The objective of the breeding program is to develop new medium-sized Impatiens cultivars with an early to medium flowering response and large rounded flowers with attractive coloration.

The new Impatiens originated from a cross-pollination made by the Inventor during the spring of 1999 of the *Impatiens hawkeri* cultivar Danikaza, not patented, as the female, or seed, parent with the *Impatiens hawkeri* cultivar Lycia, disclosed in U.S. Plant Pat. No. 10,322, as the male, or pollen, parent. The cultivar Fisnics Flame was discovered and selected by the Inventor as a flowering plant within the progeny of the stated cross-pollination in a controlled environment in Galder, Gran Canaria, Spain in April, 2000.

Asexual reproduction of the new cultivar by terminal cuttings taken in Galder, Gran Canaria, Spain, since July, 2000, has shown that the unique features of this new Impatiens are stable and reproduced true to type in successive generations.

SUMMARY OF THE INVENTION

The following traits have been repeatedly observed and are determined to be the unique characteristics of 'Fisnics Flame'. These characteristics in combination distinguish 'Fisnics Flame' as a new and distinct Impatiens cultivar:

1. Outwardly spreading and uniformly mounded plant habit; medium to tall growth habit.
2. Freely branching and freely flowering habit.
3. Dark green-colored foliage.

4. Medium to large, somewhat rounded, bright orangish red-colored flowers that are positioned just above and beyond the foliage.

Plants of the new Impatiens can be compared to plants of the female parent, the cultivar Danikaza. In side-by-side comparisons conducted by the Inventor in Hillscheid, Germany, plants of the new Impatiens differed from plants of the cultivar Danikaza in the following characteristics:

1. Plants of the new Impatiens had slightly lighter green-colored leaves than plants of the cultivar Danikaza.
2. Flowers of plants of the new Impatiens were lighter orangish red in color than flowers of plants of the cultivar Danikaza.

Plants of the new Impatiens can be compared to plants of the male parent, the cultivar Lycia. In side-by-side comparisons conducted by the Inventor in Hillscheid, Germany, plants of the new Impatiens differed from plants of the cultivar Lycia in the following characteristics:

1. Plants of the new Impatiens had slightly lighter green-colored leaves than plants of the cultivar Lycia.
2. Plants of the new Impatiens and the cultivar Lycia differed in leaf venation coloration.
3. Flowers of plants of the new Impatiens were bright orangish red in color whereas flowers of plants of the cultivar Lycia were white to pale pink and orange red bi-colored.

Plants of the new Impatiens can also be compared to plants of the cultivar BSR Bonfire Orange, disclosed in U.S. Plant Pat. No. 8,398. In side-by-side comparisons conducted by the Inventor in Hillscheid, Germany, plants of the new Impatiens differed from plants of the cultivar BSR Bonfire Orange in the following characteristics:

1. Plants of the new Impatiens were taller than and not as broad as plants of the cultivar BSR Bonfire Orange.
2. Plants of the new Impatiens were more freely branching than plants of the cultivar BSR Bonfire Orange.
3. Plants of the new Impatiens had broader and slightly lighter green-colored leaves than plants of the cultivar BSR Bonfire Orange.
4. Plants of the new Impatiens had larger flowers than plants of the cultivar BSR Bonfire Orange.
5. Flowers of plants of the new Impatiens were slightly darker in color than flowers of plants of the cultivar BSR Bonfire Orange.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisnics Flame' grown in a container.

DETAILED BOTANICAL DESCRIPTION

The cultivar Fisnics Flame has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers in late February and the aforementioned photograph and following observations and measurements were taken about 11 weeks later in early May. During the production of the plants, day temperatures were about 18 to 22° C. and night temperatures were about 16 to 18° C. In the following description, color references are made to The Royal Horticultural Society Colour Chart, 1995 Edition, except where general terms of ordinary dictionary significance are used.

Botanical classification: *Impatiens hawkeri* cultivar Fisnics Flame.

Parentage:

*Female parent.*—*Impatiens hawkeri* cultivar Danikaza, not patented.

*Male parent.*—*Impatiens hawkeri* cultivar Lycia, disclosed in U.S. Plant Pat. No. 10,322.

Propagation:

*Type cutting.*—Terminal tip cuttings.

*Time to initiate roots.*—Summer: About 8 to 10 days at 24° C. Winter: About 12 to 15 days at 21° C.

*Time to produce a rooted cutting.*—Summer: About 15 days at 24° C. Winter: About 18 to 20 days at 21° C.

*Root description.*—Numerous, fibrous, and freely branching; 158D to 179D in color.

Plant description:

*General appearance.*—Outwardly spreading and uniformly mounded plant growth habit; medium to tall growth habit; freely branching habit, dense and bushy appearance; freely flowering. Moderately vigorous to vigorous.

*Crop time.*—From a rooted cutting, about 9 to 10 weeks are required to produce finished flowering plants in 12-cm containers.

*Plant height.*—About 25.5 cm.

*Plant diameter or spread.*—About 40 to 45 cm.

*Lateral branches.*—Quantity per plant: About 10 to 12. Length: About 24 to 26 cm. Diameter: About 6 to 8 mm. Internode length: About 6 to 8 cm. Texture: Smooth, glabrous. Color: 180A.

*Foliage description.*—Arrangement: Primarily in whorls. Length: About 11 to 13 cm. Width: About 5.5 to 6 cm. Shape: Elliptic to ovate. Apex: Acute to acuminate. Base: Acute. Margin: Serrulate with ciliation. Texture: Smooth, slightly rugose; glabrous. Color: Developing foliage, upper surface: 139A. Developing foliage, lower surface: 185B. Fully expanded foliage, upper surface: 137A to 139A. Fully expanded foliage, lower surface: 185B to 185C. Venation, upper surface: 47A. Venation, lower surface: 53D. Petiole: Length: About 1.5 to 2 cm. Diameter: About 3 mm. Texture: Smooth, glabrous. Color, upper surface: 47A. Color, lower surface: 53D.

Flower description:

*Flower type and flowering habit.*—Single, somewhat rounded, medium to large, and orangish red-colored flowers. Freely and continuously flowering; usually about 6 to 8 flowers and flower buds per lateral branch. Flowers positioned just above and beyond the foliage; flowers typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 weeks after planting.

*Flower buds.*—Length: About 2.1 cm. Diameter: About 1.8 cm. Shape: Ovoid. Color: 40A to 40B.

*Flower length.*—About 6.5 cm.

*Flower width.*—About 6.5 to 7 cm.

*Flower depth.*—About 1 to 1.5 cm.

*Petals.*—Quantity: Five per flower, imbricate. Length: Banner petals: About 2.4 to 2.6 cm. Lateral and base petals: About 2.9 to 3.1 cm. Width: Banner petal: About 3 to 3.2 cm. Lateral and base petals: About 2.9 to 3.3 cm. Shape: Cordate. Apex: Moderately lobed, emarginate. Base: Attenuate. Margin: Entire. Aspect: Flat to slightly cupped. Texture: Smooth; satiny. Color: When opening, upper surface: 44A. When opening, lower surface: 40B. Fully opened, upper surface: 40A. Fully opened, lower surface: 40B.

*Spur.*—Quantity: One per flower. Length: About 4.5 to 5 cm. Diameter: At apex: About 0.5 mm. At flower: About 3 mm. Aspect: Curved. Color: 53D.

*Peduncles.*—Length: About 5.5 to 6 cm. Diameter: About 2 mm. Texture: Smooth, glabrous. Strength: Strong, flexible. Color: 179B.

*Reproductive organs.*—Androecium: Stamen number: Five fused at anthers, hooded; filaments free. Anther length: About 5 mm. Anther shape: Obovate. Anther color: 46C. Pollen amount: Moderate. Pollen color: 8D. Gynoecium: Pistil quantity: One per flower. Pistil length: About 5 to 6 mm. Stigma color: 53D. Style color: 53D. Ovary: Five-celled. Ovary color: Initially 139A, becoming 183A with development.

*Seed/fruit.*—Seed and fruit development has not been observed.

Disease/pest resistance: Plants of the new Impatiens have not been observed to be resistant to pathogens and pests common to Impatiens.

Low temperature tolerance: Plants of the new Impatiens have been observed to tolerate night temperatures of 5° C. with 10° C. day temperatures.

It is claimed:

1. A new and distinct cultivar of New Guinea Impatiens plant named 'Fisnics Flame', as illustrated and described.

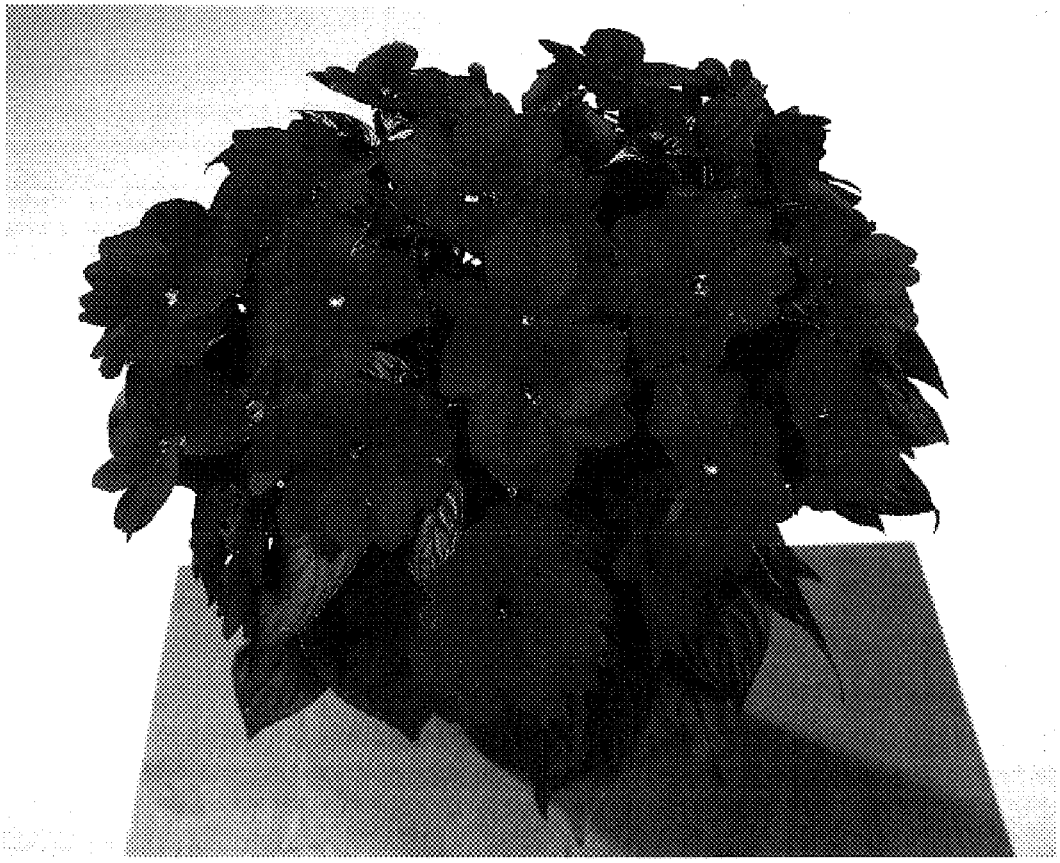

* * * * *